US008050766B2

(12) United States Patent
Zealear (10) Patent No.: US 8,050,766 B2
(45) Date of Patent: Nov. 1, 2011

(54) RESPIRATORY TRIGGERED, BILATERAL LARYNGEAL STIMULATOR TO RESTORE NORMAL VENTILATION IN VOCAL FOLD PARALYSIS

(75) Inventor: David L. Zealear, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 12/858,182

(22) Filed: Aug. 17, 2010

(65) Prior Publication Data

US 2010/0312302 A1    Dec. 9, 2010

Related U.S. Application Data

(63) Continuation of application No. 11/388,789, filed on Mar. 24, 2006, now Pat. No. 7,805,195.

(60) Provisional application No. 60/664,729, filed on Mar. 24, 2005.

(51) Int. Cl.
*A61N 1/00* (2006.01)
(52) U.S. Cl. ............................................ 607/42; 607/50
(58) Field of Classification Search .................... 607/42, 607/50
See application file for complete search history.

(56) References Cited

U.S. PATENT DOCUMENTS

| | | | |
|---|---|---|---|
| 4,830,008 A | 5/1989 | Meer | |
| 5,897,579 A | 4/1999 | Sanders et al. | |
| 6,030,350 A | 2/2000 | Jiang et al. | |
| 6,205,361 B1 | 3/2001 | Kuzma et al. | |
| 6,572,543 B1 | 6/2003 | Christopherson et al. | |
| 7,069,082 B2 | 6/2006 | Lindenthaler | |
| 7,805,195 B2 | 9/2010 | Zealear | |
| 2004/0106874 A1 | 6/2004 | Eigler et al. | |
| 2004/0215290 A1* | 10/2004 | Zealear | 607/50 |
| 2005/0165457 A1* | 7/2005 | Benser et al. | 607/42 |
| 2006/0282127 A1 | 12/2006 | Zealear | |

OTHER PUBLICATIONS

Notification Concerning Transmittal of International Preliminary Report on Patentability (Chapter I of the Patent Cooperation Treaty) No. PCT/US2006/10784 dated Nov. 22, 2007.
Notification of Transmittal of the International Search Report and the Written Opinion of the International Searching Authority, or the Declaration, corresponding to PCT Application No. PCT/US06/10784 dated Sep. 24, 2007.
Office Action corresponding to U.S. Appl. No. 11/388,789 dated Dec. 23, 2008.

(Continued)

*Primary Examiner* — Niketa Patel
*Assistant Examiner* — Catherine Voorhees
(74) *Attorney, Agent, or Firm* — Jenkins, Wilson, Taylor & Hunt, P.A.

(57) ABSTRACT

A laryngeal stimulation system including a sensor for detecting an occurrence of a respiratory signal in a subject and a laryngeal stimulator adapted for coupling to a laryngeal muscle and operable to stimulate the laryngeal muscle in response to the sensor detecting the occurrence of the respiratory signal is provided. A method for laryngeal stimulation including detecting an occurrence of a respiratory signal in a subject and then stimulating a laryngeal muscle in response to detecting the occurrence of the respiratory signal is also provided.

6 Claims, 6 Drawing Sheets

OTHER PUBLICATIONS

Office Action corresponding to U.S. Appl. No. 11/388,789 dated Aug. 4, 2009.

Zealear et al., "The biocompatibility, integrity, and positional stability of an injectable microstimulator for reanimation of the pralyzed larynx," IEEE Transactions on Biomedical Engineering, vol. 48, No. 8, pp. 890-897 (2001).

Zealear et al., "Electrically Stimulated Glottal Opening Combined with Adductor Muscle Botox Blockade Restores Both Ventilation and Voice in a Patient with Bilateral Laryngeal Paralysis," Ann. Otol. Rhinol. Laryngol., vol. 111, pp. 500-506 (2002).

Zealer et al., "Reanimation of the paralyzed human larynx with an implantable electrical stimulation device," Laryngoscope, vol. 113, No. 7, pp. 1149-1156 (2003).

* cited by examiner

PHRENIC NERVE TRIPOLAR CUFF
FIG. 4A

TRUE TRIPOLE AMPLIFIER
FIG. 4B

PRESSURE TRANSDUCER CHAMBER
FIG. 4C

RESPIRATORY TRIGGERED, BILATERAL LARYNGEAL STIMULATOR TO RESTORE NORMAL VENTILATION IN VOCAL FOLD PARALYSIS

CROSS-REFERENCE TO RELATED APPLICATIONS

This application is a continuation of U.S. patent application Ser. No. 11/388,789 filed Mar. 24, 2006 now U.S. Pat. No. 7,805,195, which claims the benefit of U.S. Provisional Application No. 60/664,729 filed Mar. 24, 2005; the disclosures of each of which are incorporated herein by reference in their entirety.

GOVERNMENT INTEREST

The presently disclosed subject matter was made with U.S. Government support under Grant No. RO1 DC001149 awarded by National Institutes of Health, and under Grant No. DC008429 awarded by National Institutes of Health. Thus, the U.S. Government has certain rights in the subject matter.

TECHNICAL FIELD

The presently disclosed subject matter relates to laryngeal stimulation systems and methods of using the same. In particular embodiments, the presently disclosed subject matter relates to a laryngeal stimulation system that can provide independent bilateral stimulation of multiple laryngeal muscles in response to detection of a respiratory signal in a subject and methods of using the system for stimulating laryngeal muscles, particularly as applied to inducing abduction of vocal folds to facilitate normal breathing.

ABBREVIATIONS

° C.=degrees Celsius
BVFP=bilateral vocal fold paralysis
EMG=electromyographic
ENG=electroneurographic
FES=functional electrical stimulation
g=grams
h=hours
kg=kilograms
M=molar
mL=milliliters
mm=millimeters
mM=millimolar
PCA=posterior cricoarytenoid
RLN=recurrent laryngeal nerve

BACKGROUND

Bilateral laryngeal paralysis is a serious and often life-threatening clinical condition. The recurrent laryngeal nerve (RLN) carries motor fibers that innervate both the abductor (posterior cricoarytenoid, PCA) muscle and adductor muscles of the vocal folds. Damage to the nerve compromises both of these functions and arrests the vocal folds in a near-closed position. In cases of bilateral vocal fold paralysis (BVFP), voice tends to be functional but airway embarrassment is often severe enough to warrant emergency tracheotomy to relieve inspiratory stridor and dyspnea.[1,2] If spontaneous recovery from nerve injury does not occur within one year, it is likely the patient will be chronically paralyzed. In such instances, long-term tracheostomy could be considered. Unfortunately, permanent tracheostomy is known to have the complications of tracheal stenosis, chronic infection, and psycho-social impairment.[3-5]

For this reason, laryngeal surgery is usually recommended to enlarge the airway and restore breathing through the mouth. Procedures such as arytenoidectomy and cordotomy, regarded as the standard of care for enlarging the airway, also have inherent complications [6-9]. Specifically, they destroy voice and compromise airway protection during swallowing.

As such, there is presently an unmet need for improved therapies for the treatment of laryngeal paralysis to facilitate return of normal ventilation.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In accordance with the presently disclosed subject matter, a laryngeal stimulation system is provided. In some embodiments, all or part of the system is implantable within the subject. In some embodiments, the laryngeal stimulation system comprises a sensor for detecting an occurrence of a respiratory signal in a subject and a laryngeal stimulator adapted for coupling to a laryngeal muscle and operable to stimulate the laryngeal muscle in response to the sensor detecting the occurrence of the respiratory signal. In some embodiments the respiratory signal comprises an inspiratory phase. In some embodiments, the laryngeal muscle is one or more PCA muscles. In some embodiments, the stimulator is operable to reanimate the laryngeal muscle. In some embodiments, the laryngeal muscle is one of paralyzed, denervated, synkinetically reinnervated, and combinations thereof. In some embodiments, the stimulation of the laryngeal muscle abducts vocal folds of the subject. In some embodiments, the subject suffers from bilateral vocal fold paralysis.

In some embodiments of the system, the sensor is adapted for positioning adjacent to an intrapleural space of the subject. In some embodiments, the sensor is adapted for positioning within a mediastinum of the subject. In some embodiments, the sensor is adapted for positioning within a manubrium of the subject.

In some embodiments of the system, the sensor comprises a nerve cuff adapted for attachment to a nerve of the subject, such as for example a phrenic nerve, and operable to detect action potentials of the nerve and transmit a signal to the laryngeal simulator for indicating the occurrence of an action potential. In some embodiments, the nerve cuff comprises a plurality of electrodes for detecting the action potentials of the nerve. In some embodiments, the laryngeal stimulation system comprises electrical circuitry coupled to the sensor for amplifying and conditioning the signal indicating the action potential. Further, in some embodiments, the sensor is adapted to indicate the occurrence of an action potential in response to the action potential having a predetermined relationship with respect to a threshold.

In some embodiments of the system, the sensor comprises a differential pressure transducer adapted to detect a pressure difference between intrapleural pressure of the subject and atmospheric pressure, wherein the difference indicates the occurrence of the respiratory signal.

In some embodiments of the system, the laryngeal muscle is a first laryngeal muscle, the stimulator is adapted for attachment to a second laryngeal muscle, and the stimulator is operable to stimulate the first laryngeal muscle and the second laryngeal muscle in response to the sensor detecting the occurrence of the respiratory signal.

In some embodiments of the system, the stimulator is operable to provide electrical stimulation to the laryngeal muscle.

In some embodiments of the system, the stimulator comprises first and second electrically-conductive rods adapted for insertion into the first and second laryngeal muscles, respectively, and wherein the first and second electrically-conductive rods are operable to emit an electrical signal for stimulating the first and second laryngeal muscles, respectively.

In some embodiments of the system, the stimulator is operable to provide independent bilateral stimulation of the first laryngeal muscle and the second laryngeal muscle in response to the sensor detecting the occurrence of the respiratory signal with respect to each muscle.

In some embodiments of the system, the stimulator comprises a plurality of electrodes operable to emit an electrical signal for stimulating the laryngeal muscle. In some embodiments, the stimulator comprises an electrode array operable to emit an electrical signal for stimulating the laryngeal muscle. Further, in some embodiments, the stimulator comprises a paddle-shaped body including a first side, and wherein the electrode array is arranged on the first side of the paddle-shaped body. Still further, in some embodiments, the electrode array is arranged in a plurality of columns.

In some embodiments of the system, the stimulator comprises a pulse generator for emitting electrical pulses to stimulate the laryngeal muscle in response to the sensor detecting the occurrence of the respiratory signal. In some embodiments, the emitted electrical pulses are square-wave pulses. Further, in some embodiments, the square-wave pulses include pulse durations from about 1 to about 2 milliseconds. Still further, in some embodiments, the emitted electrical pulses are emitted at a frequency of from about 30 to about 40 pulses per second and in some embodiments the pulses have an amplitude ranging from about 2 milliamps to about 20 milliamps.

In some embodiments, the system further comprises a timer for determining whether the respiratory signal is detected within a predetermined time interval, and the laryngeal stimulator is adapted to stimulate the laryngeal muscle in response to the timer not detecting the occurrence of the respiratory signal within the predetermined time interval.

In another embodiment of the presently disclosed subject matter, a method for laryngeal stimulation is provided. In some embodiments, the method comprises detecting an occurrence of a respiratory signal in a subject and then stimulating a laryngeal muscle in response to detecting the occurrence of the respiratory signal. In some embodiments, the respiratory signal comprises an inspiratory phase. In some embodiments, stimulation of the laryngeal muscle abducts vocal folds of the subject. In some embodiments, the laryngeal muscle is a PCA muscle. Further, in some embodiments, the laryngeal muscle is paralyzed, denervated, synkinetically reinnervated, or combinations thereof. In some embodiments, the subject suffers from BVFP.

In some embodiments, detecting the occurrence of a respiratory signal comprises detecting action potentials of a nerve, such as for example a phrenic nerve, for indicating the occurrence of the respiratory signal. In some embodiments of the method, detecting the respiratory signal comprises positioning a sensor adjacent the nerve for detecting the action potentials of the nerve. In some embodiments, detecting the respiratory signal further comprises indicating the occurrence of an action potential when the action potential has a predetermined relationship with respect to a threshold.

In some embodiments, detecting the occurrence of a respiratory signal comprises detecting a pressure difference between intrapleural pressure of the subject and atmospheric pressure, wherein the difference indicates the occurrence of the respiratory signal.

In some embodiments of the method, stimulating the laryngeal muscle comprises reanimating the laryngeal muscle in response to detecting the occurrence of the respiratory signal. In some embodiments, stimulating the laryngeal muscle comprises electrically stimulating the laryngeal muscle. In some embodiments, the laryngeal muscle is a first laryngeal muscle and a second laryngeal muscle, and comprising stimulating both first and second laryngeal muscles in response to detecting the occurrence of the respiratory signal. In some embodiments, an electrical signal (e.g., electrical pulses) is emitted for stimulating the first and second laryngeal muscles. Further, in some embodiments, the first and second laryngeal muscles are stimulated independently. In particular, in some embodiments, independent bilateral stimulation of the first laryngeal muscle and the second laryngeal muscle in response to the sensor detecting the occurrence of the respiratory signal is provided.

In some embodiments of the method, the electrical signals emitted are electrical pulses, which are square-wave pulses. In some embodiments, the square-wave pulses include pulse durations from about 1 millisecond to about 2 milliseconds. In some embodiments, the electrical pulses are emitted at a frequency ranging from about 30 pulses per second to about 40 pulses per second and in some embodiments, the pulses have an amplitude ranging from about 2 milliamps to about 20 milliamps.

In some embodiments, the method further comprises determining whether the respiratory signal is detected by a timer within a predetermined time interval, and comprising stimulating the laryngeal muscle in response to the timer not detecting the occurrence of the respiratory signal within the predetermined time interval.

Accordingly, it is an object of the presently disclosed subject matter to provide a respiratory triggered, bilateral laryngeal stimulation system to restore normal ventilation in vocal fold paralysis. This object is achieved in whole or in part by the presently disclosed subject matter.

An object of the presently disclosed subject matter having been stated above, other objects and advantages will become apparent to those of ordinary skill in the art after a study of the following Description of the presently disclosed subject matter and non-limiting Examples.

BRIEF DESCRIPTION OF THE DRAWINGS

FIGS. 4A-4C illustrate several embodiments of sensors for detecting respiratory signals.

FIGS. 6A and 6B show endoscopic video still-frames of the glottis in a patient with BVFP. Oscillographic recordings from the chest wall transducer (top trace), threshold detector (middle trace) and pulse generator (bottom trace) are superimposed on each frame of FIGS. 6A and 6B. A black arrow indicates when a still-frame was obtained relative to the phase of respiration shown in the belt transducer recording: FIG. 6A shows peak expiration; and FIG. 6B shows peak inspiration. White arrows identify the glottal edge.

DETAILED DESCRIPTION

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a muscle" (e.g., "a PCA muscle") includes a plurality of such muscles (e.g., a plurality of PCA muscles), and so forth.

Unless otherwise indicated, all numbers expressing quantities of ingredients, reaction conditions, electrical measurements and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, quantity, volume, current, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified value, as such variations are appropriate.

I. Laryngeal Stimulation System

The presently disclosed subject matter provides a system or device to restore "normal ventilation" (i.e., meet respiratory needs) by relieving airway obstruction in a subject due to, for example, impairment of mobility of the vocal folds, including bilateral impairment, using an implantable (optionally, totally implantable) laryngeal stimulation system.

The terms "subject" and "patient" are used interchangeably herein and each term refers preferably to a vertebrate subject or patient. A representative vertebrate is warm-blooded; a representative warm-blooded vertebrate is a mammal. A representative mammal is a human. As used herein, the terms "subject" and "patient" include both human and animal subjects. Thus, veterinary therapeutic uses are provided in accordance with the presently disclosed subject matter.

As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses and show horses), poultry, and the like.

The phrase "impairment of mobility of the vocal folds" refers to a decreased ability of the vocal cords to abduct, such decrease being sufficient to result in respiratory compromise of the patient, which is manifested by the subjective symptom of shortness of breath and/or the objective clinical signs of stridor and restricted peak inspiratory flow. Bilateral vocal fold paralysis (BVFP) is one non-limiting example of an impairment of mobility of the vocal folds, as the term is used herein. The impairment of mobility can result from a deficit in nerve or muscle or both. For example, but not by way of limitation, the impairment can result from laryngeal muscle paralysis, denervation, synkinetic reinnervation, and combinations thereof.

The phrases "meet respiratory needs" and "normal ventilation" refer to the amount of ventilation necessary and/or desirable to satisfy the patient's oxygen requirements and/or render the patient subjectively comfortable during periods of resting or aerobic stress, such as periods of exertion, emotional excitement, exposure to high altitude, etc.

Normal ventilation can be restored in both timing and magnitude using a laryngeal stimulation system of the presently disclosed subject matter. In some embodiments the laryngeal stimulation system comprises a respiratory sensor, which can detect the occurrence of a respiratory signal in a subject, such as for example the initiation of the inspiratory phase of respiration, and a laryngeal muscle stimulator adapted for coupling to a laryngeal muscle, including one or more nerves or nerve terminals that innervate the laryngeal muscle. The laryngeal stimulator can stimulate the laryngeal muscle to which it is coupled in response to the sensor detecting the occurrence of the respiratory signal. Thus, "stimulating a laryngeal muscle" as the phrase is used herein refers to stimulating the laryngeal muscle directly and/or stimulating the laryngeal muscle by stimulation of one or more nerves, nerve branches, or nerve terminals that innervate the laryngeal muscle (e.g., with regard to PCA muscles, the superior laryngeal nerve, the recurrent laryngeal nerve, and branches therefrom). In some embodiments, the laryngeal stimulator comprises an electrode array which directly contacts the laryngeal muscle and/or one or more nerves that innervate the muscle and transmits a stimulating electrical impulse to the muscle, and a multiprogrammable pulse generator which emits electrical pulses transmitted to the muscle and/or an innervating nerve by the electrode array. In a particular embodiment, the stimulator terminates in a body to which the electrode array is positioned, wherein the body is either rod-shaped or paddle-shaped and tailored to the anatomy of the one or more laryngeal muscles to be stimulated (e.g., left and right PCA muscles) for generation of a maximum response with conservation of electrical charge.

Figure 1:
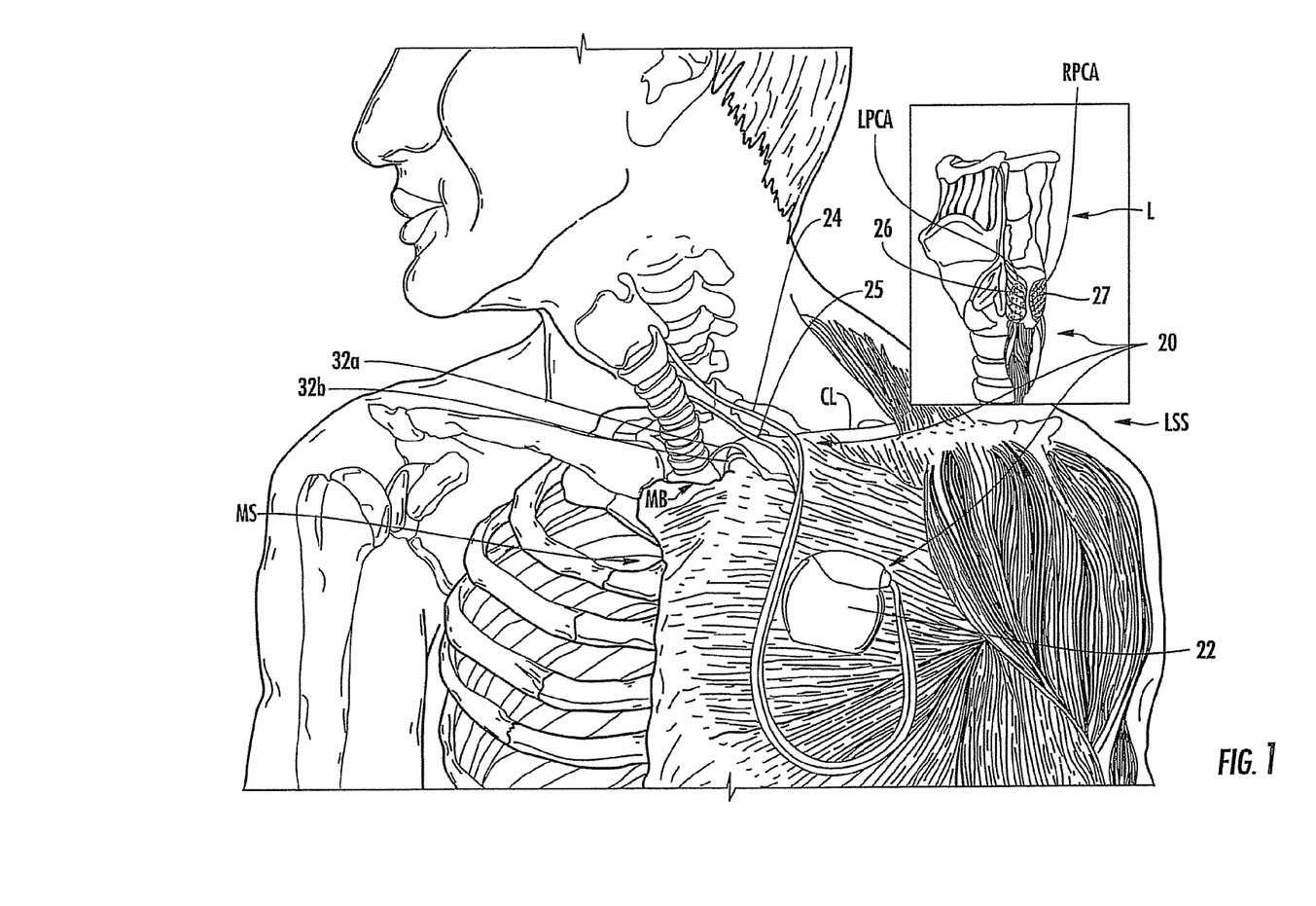
FIG. 1 is a front perspective view illustrating the laryngeal stimulation device of the presently disclosed subject matter comprising a multiprogrammable pulse generator and sensor circuits positioned in a pocket below the clavicle. The inset is a perspective view illustrating an electrode array positioned behind the PCA muscles and connected to the pulse generator for independent bilateral stimulation of the PCA muscles.
Figure 2:
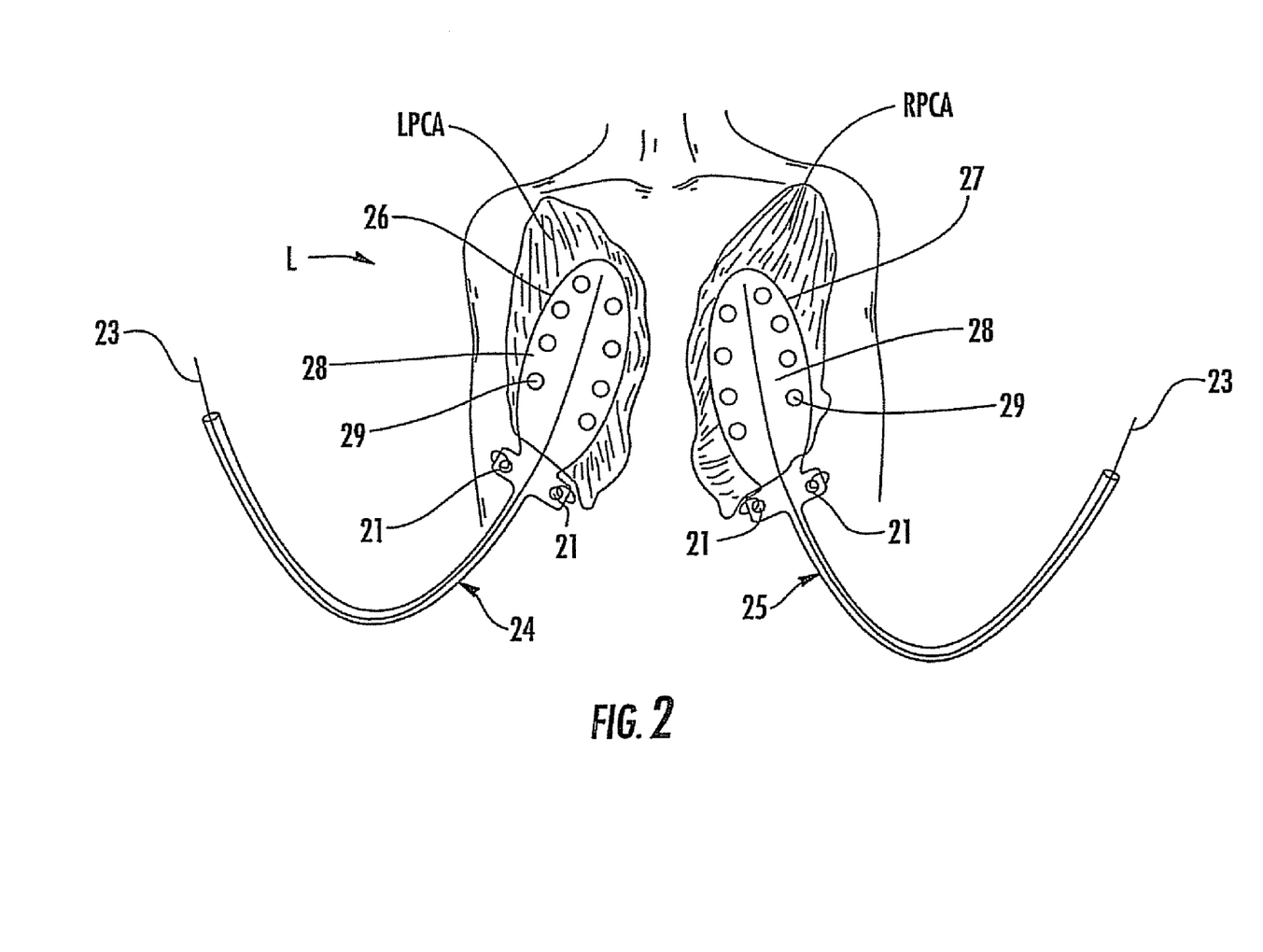
FIG. 2 is a section detailed view of a larynx illustrating one embodiment of an end of a laryngeal stimulator with paddle-shaped body comprising an electrode array of button contacts (electrodes) forming two columns on the sides of each paddle and positioned to contact either the left or right PCA muscle.

Referring now to the Figures, where like referenced characters refer to like parts throughout, FIGS. 1 and 2 illustrate one embodiment of the laryngeal stimulation system of the presently disclosed subject matter. Device LSS comprises a laryngeal stimulator 20 including a multiprogrammable pulse generator 22, to which are attached sensor circuits. Pulse generator 22 can be surgically implanted in a pocket below a clavicle CL of the patient. Device LSS further comprises a sensor (not visible in FIGS. 1 and 2; two embodiments shown in FIGS. 3 and 4) for sensing respiratory signals and relaying those signals to laryngeal stimulator 20. Three leads 24, 25, and 32 interfaced with laryngeal stimulator 20 can be tunneled to an incision in the anterior neck. A first and a second stimulus lead 24 and 25 each terminate in a rod- or paddle-shaped first and second body 26 and 27, respectively. First and second laryngeal stimulator bodies 26 and 27 comprise a first side 28 (best seen in FIG. 2) having an array of electrodes 29 arranged thereon that contacts or closely approximates the laryngeal muscle and/or innervating nerves or nerve branches. As shown in the inset of FIG. 1, first and second bodies 26 and 27 are positioned on each side of the larynx L in a subperichondrial or submuscular pocket beneath left and right PCA muscles LPCA and RPCA. The insert of FIG. 1 shows paddle-shaped bodies 26 and 27 in position following implantation. Lead 32 of device LSS further comprises first and second sensor leads 32a and 32b, each terminating in a pressure sensitive chamber 31 (not visible in FIG. 1), positioned in some embodiments in the mediastinum MS, with the active chamber (that is, the chamber that senses intrapleural pressure) near the intrapleural space and the reference chamber (that is, the chamber that senses atmospheric pressure) positioned a few centimeters away from the intrapleural space, so as not to detect any respiratory signal.

I.A. Laryngeal Muscle Stimulator

A multiprogrammable pulse generator, for example pulse generator 22 in FIG. 1, can provide independent stimulation of laryngeal muscles bilaterally. For example, pulse generator 22 can provide for independent bilateral stimulation of a first and a second laryngeal muscle, such as for example left and right PCA muscles LPCA and RPCA, to reanimate the muscles, in turn resulting in abduction of the vocal folds by both muscles and restoring ventilation to normal. The term "abduction of vocal folds" refers to that amount of abduction sufficient to permit inspiration, to relieve stridor, and/or to increase the peak inspiratory flow.

The presently disclosed laryngeal stimulation system can comprise a demand-type pacemaker functioning as a laryngeal stimulator (referred to as 20 in FIG. 1) which, when coupled with an inspiratory sensor, can sense changes in ventilatory need and adjust timing of vocal fold opening in synchrony with inspiration. Thus, one aspect of the presently disclosed laryngeal stimulation system includes the independent bilateral stimulation of first and second laryngeal muscles (e.g., left and right PCA muscles LPCA and RPCA) by a laryngeal stimulator in response to a respiratory signal (e.g., an inspiratory phase signal) detected by a respiratory sensor.

In some embodiments of the presently disclosed subject matter, a laryngeal stimulator comprising a terminal body with an electrode array having electrode contacts that are smaller and more closely spaced is provided, such as for example first and second bodies 26 and 27 comprising an array of electrodes 29 arranged on first side 28, as shown in FIG. 2. Continuing with FIG. 2, shown is a portion of larynx L with paddle-like electrode first and second bodies 26 and 27 inserted therein. Electrodes 29 can be arrayed on paddle-shaped bodies 26 and 27 forming two parallel columns on each body 26 and 27. Electrodes 29 can be "button contacts" in some embodiments. This type of paddle-shape is symmetrical and could be used for either left or right PCA muscle LPCA and RPCA. Once inserted into a PCA pocket, a column of electrode contacts can be situated optimally for activation of a synkinetically reinnervated muscle, and avoid stray activation of antagonistic adductor nerve fibers. Eyelets 21 at the base of each of first and second bodies 26 and 27 can be used as an anchor by suturing each of first and second bodies 26 and 27 to the cricoid cartilage (not shown in FIG. 2). A wire stylet 23 can be inserted through stimulus leads 24 and 25 and extended to the tip of paddle-shaped bodies 26 and 27 to give rigidity to the stimulus leads 24 and 25 and bodies 26 and 27 during insertion into the pocket. First and second bodies 26 and 27 can comprise any suitable material, including but not limited to an elastic material such as a silastic DACRON®-mesh patch (Invista North America, Wilmington, Del., U.S.A.). However, a stiffer material can also be used if greater stability and longevity is desired. Once each of first and second bodies 26 and 27 is implanted, stylet 23 can be removed.

This embodiment effectively increases the number of electrode channels available for laryngeal muscle stimulation by at least twofold over systems currently under study in the art. The additional channels provide redundancy in face of a potential shift in electrode 29 position or loss of channel, both of which have been encountered in the art. For example, in some embodiments, each electrode 29 in the electrode array can be one-and-a-half millimeters wide with one-and-a-half millimeters between channels.

Another potential disadvantage of a rod-shaped electrode used in prior art systems is that once placed in a pocket between the PCA muscle and underlying cricoid cartilage, the charge emanating from the cartilage side would be wasted. Thus, particular embodiments of the presently disclosed subject matter provide, such as those shown in FIGS. 1 and 2, an array of electrodes 29 is positioned on first side 28 of paddle-shaped body 26 or 27 of laryngeal stimulator 20, where button electrodes 29 contact against the PCA muscle LPCA or RPCA and/or innervating nerves, while the opposite surface of paddle-shaped body 26 or 27 can contain no electrodes 29. The paddle shape can prevent body 26 or 27 from rotating 180 degrees and disrupting proper alignment. In some embodiments, electrodes 29 can be arranged in two to three columns, running down a long axis of body 26 or 27 (FIG. 2). The flexibility of having more than one column of contact electrodes 29 can increase the redundancy two to three times over that of a rod-shaped electrode array. Increased number of contacts can require a decrease in button contact surface area to hold the total surface area and electrode impedance relatively constant. In some embodiments of the presently disclosed subject matter, rectangular rather than circular contact electrodes 29 are incorporated into the electrode array to minimize shunting between adjacent contact electrodes 29.

In some embodiments, multiprogrammable pulse generator, shown at 22 in FIG. 1, can include a power supply, a stimulus generation circuit, a sensor conditioning and trigger circuit, and a radio frequency receiver. Stimulation and sensor parameters can be programmed through the skin after implantation using an external programmer and radio frequency transmitter. In one embodiment, the circuits in the implantable system are powered by a non-rechargeable lithium battery (e.g., Genesis XP model, Advanced Neuromodulation Systems, Plano, Tex., U.S.A.). A calculation of charge utilization by this circuit during bilateral laryngeal muscle stimulation presently estimates battery life to be six to eight years. In another embodiment, the battery utilized can be one that is recharged through the skin, extending the lifetime to as long as twenty years. This represents a significant improvement over the power supply used in earlier clinical trials in which the battery lifespan was only approximately three and a half years.

Continuing with FIGS. 1 and 2, multiprogrammable laryngeal stimulator 20 facilitates bilateral laryngeal muscle stimulation with each muscle (e.g., each PCA muscle LPCA and RPCA) controlled independently. The prior art unifunctional stimulator devices can deliver only a single paradigm and therefore cannot activate both left and right PCA muscles LPCA and RPCA optimally where the electrode positions differ relative to their respective PCA muscle. Thus, the presently disclosed subject matter differs advantageously from the prior art in which a single stimulus paradigm is used to produce abduction on only one side of the larynx. Even though it is possible to close the tracheostomy and return breathing through the mouth with unilateral stimulation, the patient is still relegated to a relatively sedentary lifestyle. In contrast, the presently disclosed subject matter provides in some embodiments a stimulator capable of independent bilateral stimulation, which can restore a normal level of ventilation and allow the patient to lead an active lifestyle.

The presently disclosed subject matter further provides a stimulus paradigm incorporated within the laryngeal stimulator effective for activation of denervated or synkinetically reinnervated laryngeal muscles. A stimulus train of biphasic, charge-balanced square-wave pulses can be delivered to produce laryngeal muscle stimulation (e.g., PCA muscle LPCA and/or RPCA stimulation) bilaterally, resulting in contraction of the laryngeal muscle and abduction of the vocal folds during inspiration.

The pulse duration can differ from that generally used to activate innervated muscles paralyzed from a central nervous system injury. In this case, muscles are activated indirectly through their nerve terminals, and require only a short pulse duration. Based on this requirement, most commercial stimulators designed for activation of nervous tissue are programmed for pulse durations of less than 0.1-0.2 milliseconds. In the case of denervated muscle, muscle fibers must be activated directly and can require longer pulse durations of 1-2 milliseconds. In most instances, synkinetic reinnervation of laryngeal muscle also occurs. Muscle activation is mediated indirectly through nerve terminal stimulation, yet longer pulse durations are required than for that activation of normally innervated muscle. In some embodiments of the presently disclosed subject matter, longer pulse durations (e.g., about 1-2 milliseconds or longer) are beneficial for activation of denervated or synkinetically human laryngeal muscles.

In some embodiments, the pulse train can be delivered at a frequency of approximately 30-40 pulses per second to produce a fused, tetanizing contraction of the PCA muscle and a smooth abduction of the vocal fold. Further, in some embodiments, the laryngeal stimulator disclosed herein provides for a train rate that can be varied depending on the respiratory rate, with a stimulus train triggered by an inspiratory sensor. Train duration can be set by the decline of the inspiratory signal below a predetermined threshold level. In some embodiments, the stimulation duty cycle can be around 50%. However, during rapid breathing with exercise, the stimulus "on" time can be programmed to not be allowed to fall below a minimum level (e.g., about 1.0 seconds). In some embodiments, the amplitude of the stimulus required can be varied from about 2 milliamps to about 20 milliamps, in some embodiments from about 5 milliamps to about 15 milliamps, and in some embodiments from about 8 milliamps to about 12 milliamps, depending upon a number of factors, including for example the total contact surface area in apposition to a laryngeal muscle (e.g., PCA muscle LPCA and/or RPCA), the muscle-contact distance, the resistance of intervening tissue (i.e., fibrosis), and the degree of current shunting between cathode and anode poles. The parameter requirements can be varied from muscle to muscle (e.g., left and right PCA muscles LPCA and RPCA) within a patient, or between patients because of these variables. The stimulus requirements can also vary depending upon the degree of muscle denervation, reinnervation and atrophy and the laryngeal stimulation device disclosed herein can accommodate the varying requirements.

I.B. Respiratory Signal Sensor

The presently disclosed subject matter provides in some embodiments a laryngeal stimulation system comprising a respiratory signal sensor (e.g., an inspiratory sensor) for triggering and controlling one or more laryngeal muscles, including for example PCA muscles LPCA and RPCA, seen in FIGS. 1 and 2. Previous laryngeal pacing devices disclosed in the art have not been coupled to a sensor of respiration, including for example a sensor of the inspiratory drive. With prior art devices, stimulation of the PCA muscle occurs in a "free-run" configuration and is not synchronized to respiration with respect to the rate and timing of inspiration. With the prior art devices, the patient must entrain his or her breathing rate to that of the device. However, failure of entrainment poses the risk of stimulated glottal opening during voice production or swallowing, leading to interruption of speech or inhalation of food.

In contrast, the laryngeal stimulation system disclosed herein comprises a sensor for detecting respiration signals, such as inspiration, to permit stimulated glottal opening which is synchronized with inspiration. Speech interruption and aspiration can thus be avoided utilizing the presently disclosed laryngeal stimulation system. Further, the "demand-type" stimulation system disclosed herein can increase the frequency of stimulated glottal opening when respiratory rate increases during exercise or stress.

There are several sources of respiratory signal (e.g., inspiratory drive) from a subject available for monitoring that can be considered for use in time-controlled laryngeal muscle stimulation. For example, sensors have been used in acute animal experiments to actually trigger PCA muscle stimulation, however none of the trigger sites were demonstrated as practical for chronic laryngeal pacing, and all have inherent shortcomings. More specifically, diaphragm electromyographic (EMG) activity has been tested as a signal source since the diaphragm becomes active during each inspiration.

However, chronic recording from the thin muscular layer of the diaphragm with implantable electrodes is likely to be unstable.

Tracheal elongation has also been suggested as a signal source, but this action also occurs during swallowing. Stimulated glottal opening during swallowing could result in aspiration, which makes use of this source potentially dangerous. A decrease in intratracheal temperature during inspiration has been studied as a signal source in acute animal experiments. Unfortunately, an indwelling tracheal thermistor would not likely be tolerated over the long term. Measurement of chest wall expansion is another choice as a trigger for laryngeal pacing. This technology utilized an external belt transducer to trigger the external pacing circuit. Yet, an external sensor would not be a suitable candidate for a totally implantable laryngeal stimulation device. In addition, false triggering would occur with extraneous chest wall movements unrelated to inspiration.

With chest wall impedance, the resistance or impedance between two fixed points in the chest wall will increase with inflation of the chest. However, it is possible the small change in impedance might be immeasurable in a patient population with airway obstruction, such as for example as occurs in BVFP. In fact, the issue of airway obstruction can impact the feasibility of every approach mentioned hereinabove.

In subjects with airway obstruction, the rate and volume of inspired air can be nonexistent or marginal because the airway is obstructed by, for example, a paralyzed glottis. With the inability to inflate the lungs through the obstruction, there can be a compensatory increase in phrenic nerve electroneurographic (ENG) activity, an increase in diaphragm EMG activity, and an increase in intrapleural pressure negativity. As such, the presently disclosed subject matter provides sensors that can measure these respiratory signals and transmit one or more of these respiratory signals to the laryngeal stimulator, such as for example laryngeal stimulator 20 seen in FIGS. 1 and 2, for stimulation of one or more laryngeal muscles (e.g., left and right PCA muscles LPCA and RPCA in FIGS. 1 and 2), wherein the muscle stimulation results in opening of the obstructed airway (e.g., laryngeal fold abduction) and restoration of normal ventilation. As noted hereinabove, measurement of diaphragm EMG as an accurate indicator of inspiration can be difficult in certain subjects, and therefore in these subjects it may prove advantageous to utilize sensors that measure phrenic nerve ENG activity and/or intrapleural pressure negativity preferentially.

During inspiration, negative intrapleural pressure can be monitored directly from the intrapleural space, such as for example in subjects having an obstructed glottis. In some embodiments where negative intrapleural pressure is measured as a signal of respiration (e.g., the inspiration phase of respiration), the sensor (e.g., a differential pressure transducer) can be implanted in a portal made in a region of the sternum, such as for example the top portion of the sternum (i.e., the manubrium MB), affixed to the bone and sealed in place with an adhesive. Although penetrating the intrapleural space could yield a measurement with a high signal to noise ratio, it could also potentially lead to pneumothorax and lung collapse. Therefore, in some embodiments, the pressure sensor is located near, rather than within, the intrapleural space, within the mediastinum MS. Mediastinum MS, also referred to as the "interpleural space", lies between the right and left pleura in and near the median sagittal plane of the chest. It extends from the sternum in front to the vertebral column behind, and contains all the thoracic viscera excepting the lungs. Alternatively, the pressure sensor can be placed in some embodiments directly within manubrium MB. In some embodiments, the pressure sensor can be positioned within the body through a primary neck incision also used to position the laryngeal muscle stimulus arrays (see FIG. 1).

The pressure sensor can be a dual-chambered differential pressure transducer system. Each of the two chambers of the system can utilize the same type of sensor chamber to detect pressure changes at either an "active site" where inspiration signals are detected (the active chamber) and a "remote site" (reference chamber) where atmospheric pressure is measured and compared against pressure changes detected by the active chamber. The active chamber can be positioned to detect intrapleural pressure changes relative to atmospheric, while the reference chamber can be positioned more remotely, and would only detect the atmospheric pressure.

Figure 4A:
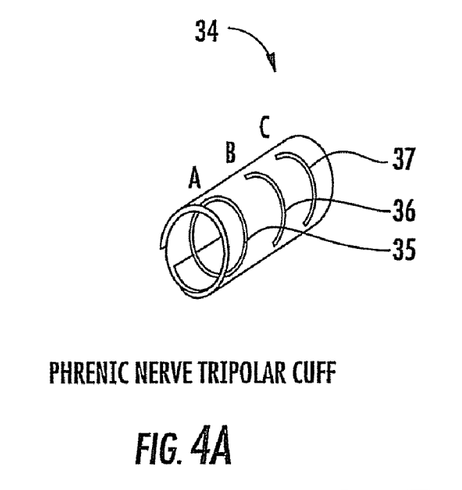
FIG. 4A is a perspective view of an exemplary nerve cuff.
Figure 4B:
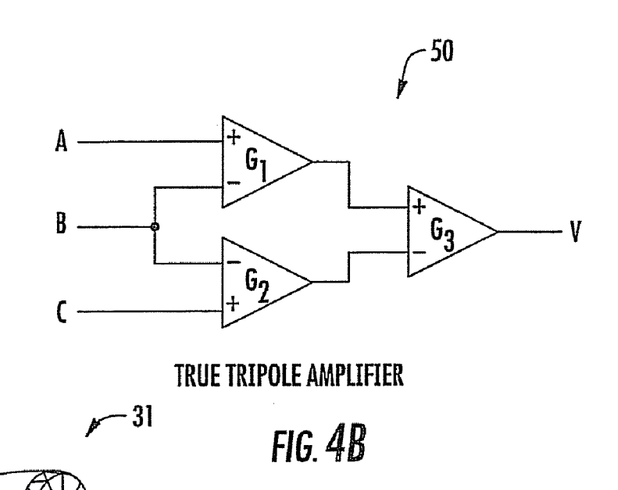
FIG. 4B is a schematic diagram of an exemplary logic circuit for determining a true respiratory signal detected by a nerve cuff. Letters A, B, and C correspond to signals generated from ring electrodes 35, 36, and 37 shown in FIG. 4A, respectively.
Figure 4C:
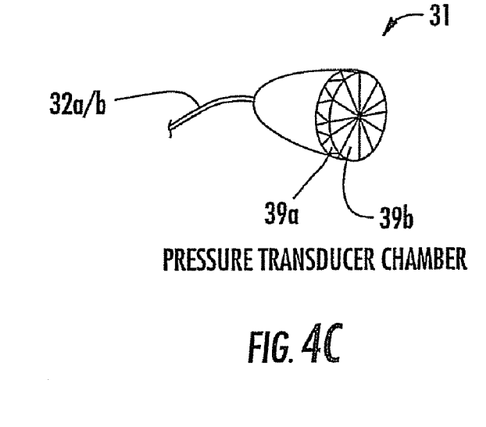
FIG. 4C is a perspective view of an exemplary pressure transducer chamber.

Referring now to FIG. 4C, an exemplary pressure transducer chamber 31 for use as either the active or reference chamber of the dual-chambered differential pressure transducer system is illustrated. Chamber 31 comprises a shell case enclosing an internal space in flow communication with an open end, which is covered with an elastic membrane 39b (e.g., a biocompatible elastic membrane) coupled to a film 39a. Membrane 39b is sensitive to pressure changes, which are transferred to piezoelectric film 39a and converted from mechanical into electrical signals. The signals are amplified and filtered by circuitry within chamber 31. The circuitry is powered by a battery in laryngeal stimulator through lead 32. The amplified and conditioned electrical signals are then transferred via lead 32a or 32b to laryngeal stimulator 20.

A differential type of pressure transducer can be particularly beneficial, as inspiratory effort can be detected in comparison to a relative atmospheric pressure rather than according to a predetermined set value. Thus, the differential pressure transducer detects a pressure difference between the interpleural pressure of the patient and the atmospheric pressure, and if a difference is detected above a chosen threshold, it is indicative of an inspiratory phase. The respiratory signal is then transmitted to the laryngeal stimulator for stimulation of the laryngeal muscles and subsequent opening of the airway to facilitate breathing. In the face of a change in atmospheric pressure, such as might occur with a change in altitude (e.g., ascendance in elevator, mountain climbing, air travel, etc.), the pressure sensor will adjust to measure a change in intrapleural pressure relevant to the new atmospheric pressure.

In some embodiments of the presently disclosed laryngeal stimulation system, a sensor comprising a nerve cuff, such as for example a phrenic nerve cuff, can be utilized for sensing inspiratory signals and for synchronous triggering of an implantable laryngeal stimulator. The phrenic nerve arises from the third, fourth, and fifth cervical spinal nerves (C3-C5). It provides motor innervation to the diaphragm and is thus responsible for the act of breathing, including stimulation of the diaphragm to initiate the inspiration phase. A nerve cuff sensor coupled to the phrenic nerve can detect action potentials of the nerve as the nerve pulse travels through the phrenic nerve to the diaphragm to initiate inspiration. The detected action potentials are registered as respiration signals by the sensor and transmitted to the laryngeal stimulator, such as for example laryngeal stimulator 20 in FIG. 1. The laryngeal stimulator then stimulates the laryngeal muscle, facilitating normal ventilation as disclosed herein.

Figure 3:
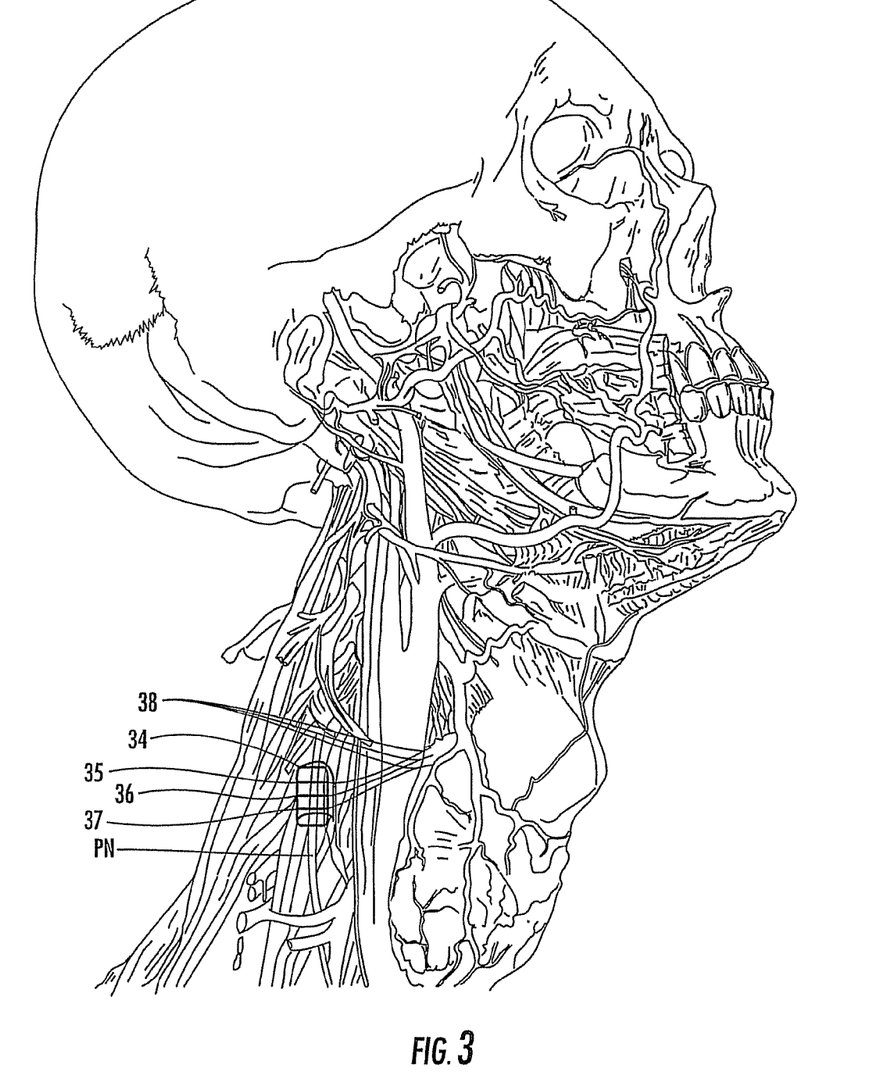
FIG. 3 is a side perspective view illustrating an implanted tripolar cuff sensor for recording ENG potentials from a phrenic nerve.

Referring now to FIGS. 3 and 4A, illustrated in FIG. 3 is a partially dissected head and neck of a human subject showing a phrenic nerve PN with a nerve cuff 34 attached to phrenic nerve PN. FIG. 4A shows a close-up perspective view of nerve cuff 34. In some embodiments, a silastic nerve cuff 34 can be utilized, which can have three equally-spaced ring electrodes 35, 36, and 37 embedded in the inside wall, as shown in FIGS. 3 and 4A, which can be connected by cuff leads 38 (FIG. 3) to pulse generator 22, as shown in FIG. 1. Cuff 34 has a single slit made along the length of the silastic tube for positioning cuff 34 around a nerve, such as for example phrenic nerve PN. In another embodiment, a self-sizing spiral cuff can be used. The self-sizing spiral cuff has a slit made in the form of a spiral, which allows it to fit around a broad range of nerves of various diameters and avoids nerve compression.

As such, a "tripolar cuff", as shown in FIGS. 3 and 4A, allows relatively large EMG potentials originating outside the cuff to be nullified, while relatively smaller ENG potentials from the nerve inside cuff 34 can be reproduced faithfully. More specifically, the EMG potential differences between central electrode 36 and first and second outer electrodes 35 and 37 are equal and opposite, and can be cancelled by differential amplifier recording. In contrast, action potentials propagating down phrenic nerve PN during inspiration would reach first outer electrode 35 and second outer electrode 37 at different times, and therefore would not cancel with differential recording, providing for an accurate measurement of nerve activity. FIG. 4B diagrams an exemplary logic circuit 50 for determining the detection of true ENG potentials.

For embodiments utilizing nerve cuff sensor 34, the conditioning and trigger circuit can include a quasi-tripole or a true-tripole type of amplifier (FIG. 4B) incorporated in electrical circuitry, which is connected to cuff leads 38. If interference from EMG activity does not cancel because of cuff imbalances due to asymmetrical tissue ingrowth into cuff 34, then an adaptive type EMG amplifier can be substituted. The amplified output signal can be rectified and integrated following the amplifier and filter (see FIG. 5). In this manner, the summated activity from axons during an inspiratory burst can be integrated and fed into the next component in sequence, a threshold detector. The threshold level can be set low enough to provide a gated PCA muscle stimulation and glottal opening sufficient for ventilation, but high enough to prevent any mistriggering of stimulation. For example, the threshold can be set high enough to avoid false triggering of stimulation by EMG noise or chest wall movements, resulting in aspiration or voice interruption. Further, the threshold can be set low enough to trigger stimulation during unambiguous inspiratory efforts, identified, for example, by recording of intratracheal pressure from a patient's tracheostoma or intercostal muscle EMG.

Figure 5:
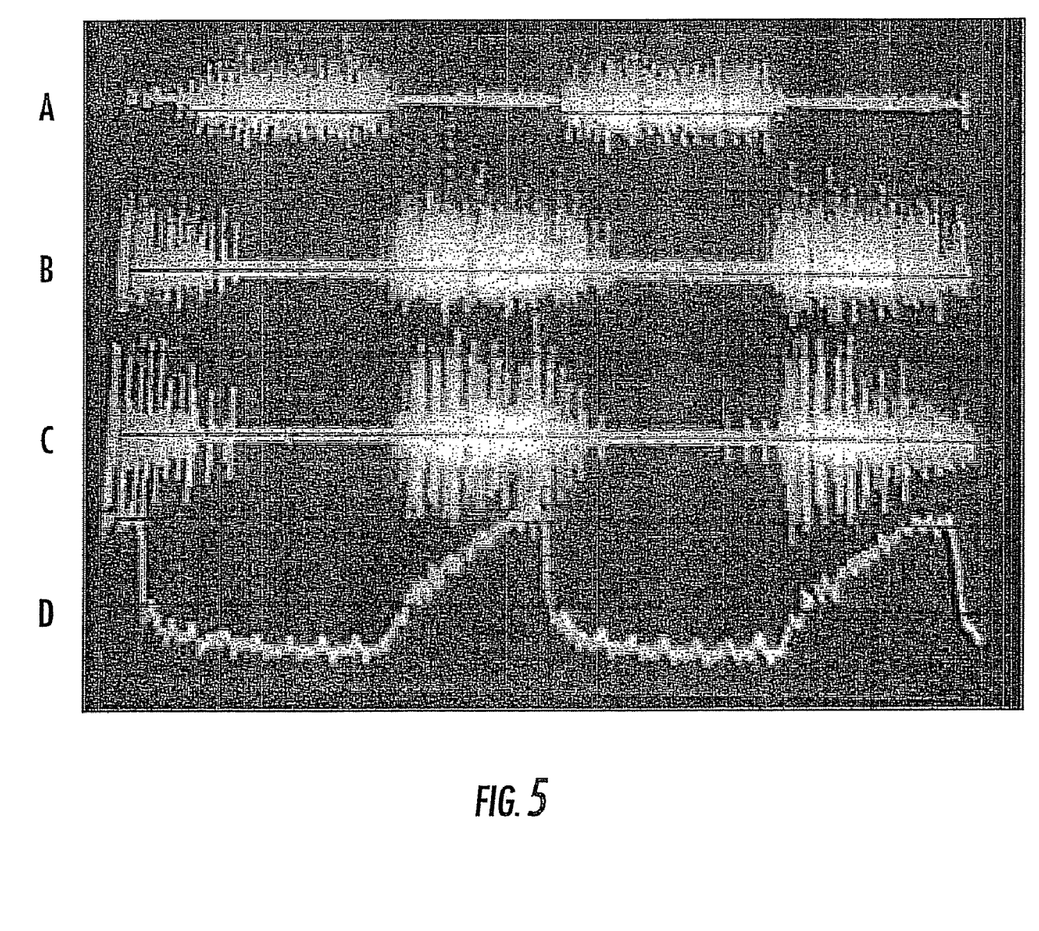
FIGS. 5A-5D are a series of oscillographic recordings from the external intercostal muscle (FIG. 5A), PCA muscle (FIG. 5B), and phrenic nerve (FIG. 5C) in a canine subject. The trace in FIG. 5D shows the rectified and integrated recording of the phrenic nerve activity, which can be inputted into the threshold detector.

FIG. 5 shows a series of oscillographic recordings from the external intercostal muscle (FIG. 5A), PCA muscle FIG. 5B), and phrenic nerve FIG. 5C) in a canine model. The trace shown in FIG. 5D provides the rectified and integrated recording of the phrenic nerve activity, which would be inputted into the threshold detector. The similarity in timing between the PCA and phrenic nerve activity confirms the applicability of measuring phrenic nerve action potentials as an appropriate inspiratory trigger signal.

Figure 6A:
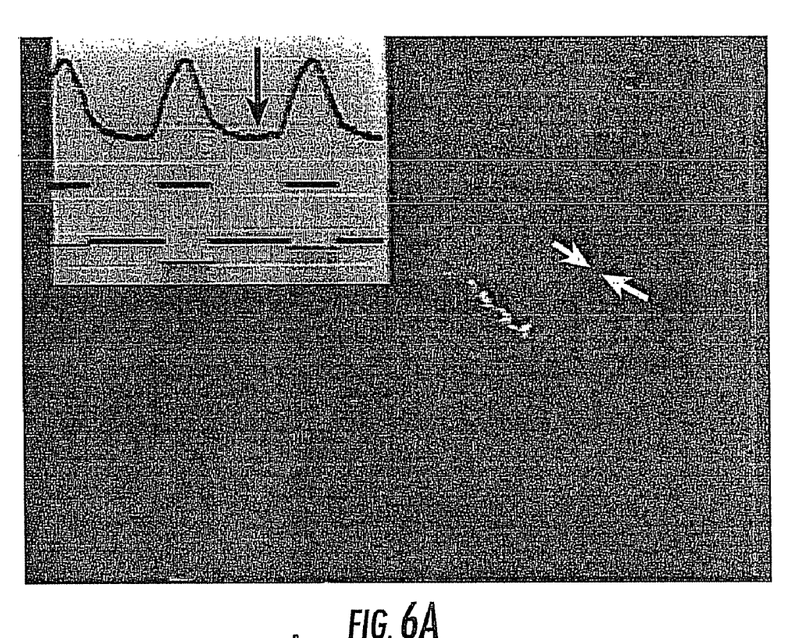
Figure 6B:
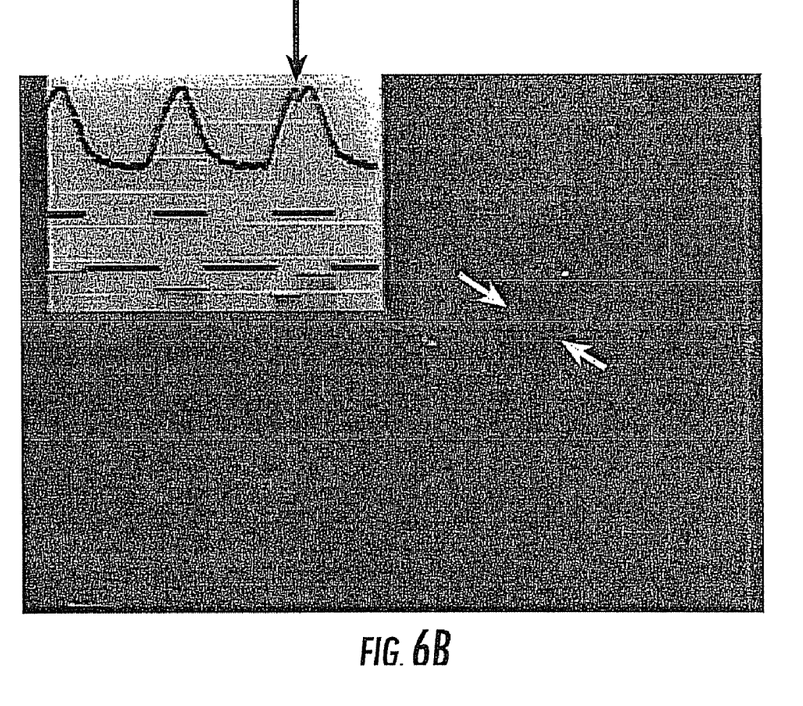

FIG. 6 shows stimulated abduction of the left vocal fold in a BVFP patient under the control of a chest wall expansion sensor and threshold detector circuit. While a chest wall expansion sensor may not be the preferred sensor in many BVFP patients for long-term treatment for the reasons previously stated, the figure demonstrates that stimulated glottal opening can be triggered and timed with inspiratory effort. For the phrenic nerve cuff embodiment, amplified-filtered, rectified-integrated signals can be substituted and inputted into the threshold detector to activate glottal opening. For the pressure transducer embodiment, signals from the dual-chambered pressure transducer can be fed into a differential amplifier, band-pass filtered, and inputted into the threshold detector.

In some embodiments, the sensor conditioning and trigger circuit parameters can have the flexibility to be changed telemetrically through the skin. Thus, threshold levels, amplifier gains, etc. can be changed by the external transmitter after implantation. This can be beneficial as it allows for variation in the sensor sensitivity across patients or over time in a given patient should, for example, partial encapsulation or migration of the sensor occur, weakening the signal.

To reiterate, in some embodiments, particularly those in which a subject suffers from airway obstruction due to for example BVFP, the respiratory sensor utilized in the presently disclosed laryngeal stimulation system can be selected based on detection specificity of compensatory changes in the respiration of the subject due to the airway obstruction. As previously noted, airway obstruction can result in compensatory respiration changes including increases in neuromuscular drive (e.g., phrenic, diaphragm) and negative airway pressure. The sensors utilized in the laryngeal stimulation system disclosed herein can therefore include sensors which can detect a respiratory signal based on these compensatory respiration changes, including for example nerve cuff sensors (e.g., phrenic nerve cuff sensor 34) that measure action potentials in the monitored nerve and pressure sensor systems (e.g., dual differential pressure transducer sensors 31) that detect pressure differences between intrapleural pressures of the subject and atmospheric pressure.

I.C. Respiratory Signal Timer

In some embodiments of the presently disclosed system, laryngeal muscle stimulation continues even in the absence of a sensor signal. For example, a timer can be incorporated into the system that measures a time period between respiratory signals. If no signal is detected within a predetermined time interval, such as for example between about 5 seconds and about 10 seconds, the multiprogrammable stimulator (referred to as 22 in FIG. 1) can default to a free run format until the sensor signaling falls again within the desired interval. This default feature can be a beneficial safety feature in case of failure of the sensor or loss of its capacity to detect inspiratory events.

II. Methods for Laryngeal Stimulation

The presently disclosed subject matter provides a laryngeal stimulation system as disclosed herein, which can be utilized for stimulation of one or more laryngeal muscles. The system has particular applicability for use with subjects suffering from airway obstruction due to muscular paralysis, such as resulting from for example impairment of mobility of the vocal folds, including bilateral impairment (e.g., BVFP). As such, the presently disclosed subject matter provides methods for laryngeal stimulation.

In some embodiments, the method for laryngeal stimulation comprises detecting an occurrence of a respiratory signal in a subject and then stimulating one or more laryngeal muscles in response to detecting the occurrence of the respiratory signal. In some embodiments, for example, the respiratory signal comprises an inspiratory phase. In some embodiments, stimulation of the one or more laryngeal muscles abducts vocal folds of the subject, which in turn removes the obstruction and facilitates normal ventilation. In some embodiments, the one or more laryngeal muscles are one or more PCA muscles. Further, in some embodiments, the one or more laryngeal muscles are paralyzed, denervated, synkinetically reinnervated, or combinations thereof.

In some embodiments, detecting the occurrence of a respiratory signal comprises detecting action potentials of a nerve, such as for example a phrenic nerve, for indicating the occurrence of the respiratory signal. As discussed herein, the phrenic nerve facilitates control of the diaphragm, and nerve impulses through the phrenic nerves to the diaphragm are indicative signals of the inspiration phase of respiration. Therefore, in some embodiments of the method, detecting the respiratory signal comprises positioning a sensor, such as a nerve cuff, adjacent the nerve, for example a phrenic nerve, for detecting the action potentials of the nerve. In some embodiments, detecting the respiratory signal further comprises indicating the occurrence of an action potential when the action potential has a predetermined relationship with respect to a threshold, that is, when the action potential reaches a magnitude above a predetermined threshold that is indicative of a true respiratory signal.

In some embodiments, detecting the occurrence of a respiratory signal comprises detecting a pressure difference between intrapleural pressure of the subject and atmospheric pressure, wherein the difference indicates the occurrence of the respiratory signal. In some embodiments, a differential pressure transducer can be utilized to detect the pressure difference.

In some embodiments of the method, stimulating one or more laryngeal muscles comprises reanimating the one or more laryngeal muscles in response to detecting the occurrence of a respiratory signal. For example, in some embodiments, stimulating the one or more laryngeal muscles comprises electrically stimulating the one or more laryngeal muscles. In some embodiments, the laryngeal muscles are a first laryngeal muscle and a second laryngeal muscle, both of which are stimulated in response to detecting the occurrence of the respiratory signal. In some embodiments, an electrical signal (e.g., electrical pulses) is emitted for stimulating the laryngeal muscles. Further, in some embodiments, the first and second laryngeal muscles are stimulated independently. In particular, in some embodiments, independent bilateral stimulation of the first laryngeal muscle and the second laryngeal muscle in response to the sensor detecting the occurrence of the respiratory signal is provided.

In some embodiments of the method, the electrical signals emitted are electrical pulses, which are square-wave pulses. In some embodiments, the square-wave pulses include pulse durations from about 1 to about 2 milliseconds. In some embodiments, the electrical pulses are emitted at a frequency of ranging from about 30 to about 40 pulses per second and in some embodiments, the pulses have an amplitude ranging from about 2 milliamps to about 20 milliamps, in some embodiments from about 5 milliamps to about 15 milliamps, and in some embodiments from about 8 milliamps to about 12 milliamps.

In some embodiments, the method further comprises determining whether the respiratory signal is detected by a timer within a predetermined time interval. If the signal is not detected within the time interval, then the method further comprises stimulating the laryngeal muscle in response to the timer not detecting the occurrence of the respiratory signal within the predetermined time interval.

REFERENCES

The references listed below, as well as all references cited in the specification, are incorporated herein by reference to the extent that they supplement, explain, provide a background for, or teach methodology, techniques, and/or compositions employed herein.

1. Dedo H. The paralyzed larynx: An electromyographic study in dogs and humans. *Laryngoscope* 1970, 80:1455-1517.
2. Holinger L, Holinger P C, Holinger P H. Etiology of the bilateral abductor vocal cord paralysis. *Ann Otol* 85:428-36.
3. Viau F, Ledente A, Le Tinier J Y. Complications of tracheotomy. *Rev Pneumol Clin* 1988, 44(1):24-32.
4. Goldenberg D, Ari E G, Golz A, Danino J, Netzer A, Joachims H Z. Tracheotomy complications: a retrospective study of 1130 cases. *Otolaryngol Head Neck Surg* 2000, 123(4):495-500.
5. Norwood S, Vallina V L, Short K, Saigusa M, Fernandez L G, McLarty J W. Incidence of tracheal stenosis and other late complications after percutaneous tracheostomy. *Ann Surg* 2000, 232(2):233-41.
6. Maurizi M, Paludetti F, Galli J, Cosenza A, Di Girolamo S, Ottaviani F. CO2 laser subtotal arytenoidectomy and posterior true and false cordotomy in the treatment of post-thyroidectomy bilateral laryngeal fixation in adduction. *Eur Arch Otorhinolaryngol* 1999, 256(6):291-5.
7. Eckel H E, Thumfart M, Wassermann K, Vossing M, Thumfart W F. Cordectomy versus arytenoidectomy in the management in bilateral vocal cord paralysis. *Ann Otol Rhinol Laryngol* 1994, 103(11):852-7.
8. Lawson G, Remade M, Hamoir M, Jamart J. Posterior cordectomy and subtotal arytenoidectomy for the treatment of bilateral vocal fold immobility: functional results. *J Voice* 1996, 10(3):314-9.
9. Pia F, Pisani P, Aluffi P. CO2 laser posterior ventriculocordectomy for the treatment of bilateral vocal fold paralysis. *Eur Arch Otorhinolaryngol* 1999, 256(8):403-6.
10. Zealear D L, Dedo H. Control of paralyzed axial muscles by electrical stimulation. *Acta Otolaryngol* 1977, 83:514-27.
11. Dedo H. Studies of larynx and pharynx physiology. NIH Grant Application NS06527, 1973.
12. Obert P M, Young K A, Tobey D N. Use of direct posterior cricoarytenoid stimulation in laryngeal paralysis. *Arch Otolaryngol* 1984, 110:88-92.
13. Bergmann K, Warzel H, Eckhardt H-U, Gerhardt H-J. Respiratory rhythmically regulated electrical stimulation of paralyzed laryngeal muscles. *Laryngoscope* 1984, 94:1376-80.
14. Zealear D L, Herzon G D. Progress toward the development of a chronically implantable laryngeal pacemaker. In: Fujimura O, ed. *Vocal physiology: voice production, mechanisms and functions*. New York, N.Y.: Raven Press, 1988, p. 443-8.
15. Kim G R, Choi H S, Kim G R, Hong W P, Chun Y M, Park Y J. Laryngeal pacemaker using a temperature sensor in the canine. *Laryngoscope* 1987, 97:1207-10.
16. Otto R A, Temper J, Davis W, Homeyer D, Stroble M. Coordinated electrical pacing of vocal cord abductors in recurrent laryngeal nerve paralysis. *Otolaryngol Head Neck Surg* 1985, 93:634-8.
17. Broniatowski M, Kaneo S, Jacobs G, Nose Y, Tucker H M. Laryngeal pacemaker II. Electronic pacing of the posterior cricoarytenoid muscles in the canine, *Laryngoscope* 1985, 95:1194-8.
18. Ransom S A, Herzon G D, Troyk P R, Schwan M A K. Development of an inspiratory pressure-triggered laryngeal pacer. *IEEE Trans Rehab Eng* 1995, 3(4):318-23.
19. Sanders I. Electrical stimulation of laryngeal muscle. *Otolaryngol Clin North Am* 1991, 24:1253-74.
20. Zrunek M, Streinzer W, Mayr W, Burian K, Thoma H, Gruber H. Experiments of acute and chronic direct electrical stimulation of glottis opening muscles. *Eur Arch Otorhinolaryngol* 1991, 248:445-8.
21. Zealear D L, Billante C L, Chongkolwatana C, Rho Y S, Hamdan A L, Herzon G D. The effects of chronic electrical stimulation on laryngeal muscle physiology and histochemistry. *J. Oto-Rhino-Laryngology & Related Specialties* 2000, 62(2):81-86.
22. Zealear D L, Rainey C L, Herzon G D, Netterville J L, Ossoff R H. Electrical pacing of the paralyzed human larynx. *Ann Otol Rhinol Laryngol* 1996; 105(9):689-93.
23. Zealear D L, Billante C R, Courey M S, Netterville J L, Paniello R C, Sanders I, Herzon G D, Goding G S, Mann W, Ejnell H, Herzon G D, Habets A M M C, Testerman R, Van de Heyning P. Reanimation of the paralyzed human larynx with an implantable electrical stimulation device. *Laryngoscope* 2003 July; 113(7):1149-56.
24. Billante C R, Zealear D L, Courey M S, Netterville J L. Effect of chronic electrical stimulation of laryngeal muscle on voice. *Ann Otol Rhinol Laryngol* 2002; 111:328-32.
25. Zealear D L, Swelstad M R, Sant'anna G D, Bannister R A, Billante C R, Rodriguez R J, Garren K C, Billante M J, Champney M S. Determination of the optimal conditions for laryngeal pacing with the Itrel II implantable stimulator. Otolaryngol Head Neck Surg 2001; 125(3):183-92.
26. Zealear D L, Billante C R, Courey M S, Sant'anna G D, Netterville J L. Electrically stimulated glottal opening combined with adductor muscle botox blockade restores both ventilation and voice in a patient with bilateral laryngeal paralysis. Ann Otol Rhinol Laryngol. 2002; 111(6):500-6.
27. Sanders I. Method of relieving airway obstruction in patients with bilateral vocal fold impairment. U.S. Pat. No. 5,897,579; Apr. 27, 1999.

It will be understood that various details of the presently disclosed subject matter may be changed without departing from the scope of the present subject matter. Furthermore, the foregoing description is for the purpose of illustration only, and not for the purpose of limitation.

What is claimed is:

1. A laryngeal stimulation system comprising:
   (a) a sensor for detecting an occurrence of a respiratory signal in a subject;
   (b) a first electrode adapted to be implanted into a first synkinetically reinnervated laryngeal muscle and a second electrode adapted to be implanted into a second synkinetically reinnervated laryngeal muscle; and
   (c) a pulse generator that is programmed to apply electrical pulses to a patient through the first and second electrodes to generate independent bilateral stimulation of the first synkinetically reinnervated laryngeal muscle and the second synkinetically reinnervated laryngeal muscle in response to the sensor detecting the occurrence of the respiratory signal with respect to each muscle.

2. The laryngeal stimulation system of claim 1, wherein the first electrode or second electrode further comprises a plurality of electrodes adapted to be implanted.

3. The laryngeal stimulation system of claim 1, wherein the first or second synkinetically reinnervated laryngeal muscle is a posterior cricoarytenoid (PCA) muscle.

4. The laryngeal stimulation system of claim 1, wherein the respiratory signal comprises an inspiratory phase.

5. The laryngeal stimulation system of claim 1, wherein the sensor is adapted to indicate the occurrence of an action potential in response to the action potential having a predetermined relationship with respect to a threshold.

6. The laryngeal stimulation system of claim 1, wherein the sensor comprises a differential pressure transducer adapted to detect a pressure difference between intrapleural pressure of the patient and atmospheric pressure, wherein the difference indicates the occurrence of the respiratory signal.

* * * * *

UNITED STATES PATENT AND TRADEMARK OFFICE
CERTIFICATE OF CORRECTION

| | | |
|---|---|---|
| PATENT NO. | : 8,050,766 B2 | Page 1 of 1 |
| APPLICATION NO. | : 12/858182 | |
| DATED | : November 1, 2011 | |
| INVENTOR(S) | : Zealear et al. | |

It is certified that error appears in the above-identified patent and that said Letters Patent is hereby corrected as shown below:

Column 1, lines 18-23 GOVERNMENT INTEREST replace "The presently disclosed subject matter was made with U.S. Government support under Grant No. RO1 DC001149 awarded by National Institutes of Health, and under Grant No. DC008429 awarded by National Institutes of Health. Thus, the U.S. Government has certain rights in the subject matter."

with --This invention was made with government support under Grant No. RO1 DC001149 awarded by National Institutes of Health, and under Grant No. DC008429 awarded by National Institutes of Health. The government has certain rights in the invention.--.

Signed and Sealed this

Seventh Day of February, 2012

David J. Kappos
*Director of the United States Patent and Trademark Office*